(12) United States Patent
Franklin et al.

US007270631B2

(10) Patent No.: US 7,270,631 B2
(45) Date of Patent: Sep. 18, 2007

(54) METHOD OF TUCKING SIDE PANELS WITH SIDE PANEL FOLD LOCATION CONTROL

(75) Inventors: Kent Allan Franklin, Appleton, WI (US); David Michael Lehner, Appleton, WI (US); Jesse Paul Sorenson, Little Chute, WI (US); Rodney Steele Gardinier, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 10/813,517

(22) Filed: Mar. 30, 2004

(65) Prior Publication Data
US 2004/0185996 A1 Sep. 23, 2004

Related U.S. Application Data

(62) Division of application No. 09/967,024, filed on Sep. 28, 2001, now Pat. No. 6,723,035.

(51) Int. Cl.
*B31F 1/08* (2006.01)
(52) U.S. Cl. .............. 493/424; 493/450; 493/313; 493/451
(58) Field of Classification Search ......... 493/418, 493/450, 313, 405, 416, 424, 423, 441, 442, 493/449, 451; 223/37, 38
See application file for complete search history.

(56) References Cited

U.S. PATENT DOCUMENTS

| 3,338,992 A | 8/1967 | Kinney |
| 3,341,394 A | 9/1967 | Kinney |
| 3,502,538 A | 3/1970 | Peterson |
| 3,502,763 A | 3/1970 | Hartmann |
| 3,542,615 A | 11/1970 | Dobo et al. |
| 3,692,618 A | 9/1972 | Dorschner et al. |
| 3,802,817 A | 4/1974 | Matsuki et al. |
| 3,849,241 A | 11/1974 | Butin et al. |
| 3,905,592 A | 9/1975 | Spencer et al. |
| 3,984,272 A | 10/1976 | Teed |
| 3,998,447 A | 12/1976 | Joa |
| 4,022,456 A | 5/1977 | Hooper et al. |
| 4,081,301 A | 3/1978 | Buell |
| 4,205,679 A | 6/1980 | Repke et al. |
| 4,340,563 A | 7/1982 | Appel et al. |
| 4,523,671 A | 6/1985 | Campbell |
| 4,610,680 A | 9/1986 | LaFleur |
| 4,614,512 A | 9/1986 | Capdeboscq |

(Continued)

FOREIGN PATENT DOCUMENTS

AU 78532/75 8/1976

(Continued)

*Primary Examiner*—Sameh H. Tawfik
(74) *Attorney, Agent, or Firm*—Pauley Petersen & Erickson

(57) ABSTRACT

A method of tucking a pair of side panels into a body portion of a pant-like garment in which the fold locations can be controlled. The garment is positioned between an upper vacuum conveyor and a lower vacuum conveyor. Opposing vacuum zones from the upper and lower conveyors hold a front region of the garment away from a back region of the garment. While the garment is in the opened, or pulled apart, position, the side panels are pushed between the front and back regions toward one another.

22 Claims, 12 Drawing Sheets

U.S. PATENT DOCUMENTS

| | | | |
|---|---|---|---|
| 4,615,695 A | 10/1986 | Cooper | |
| 4,663,220 A | 5/1987 | Wisneski et al. | |
| 4,665,306 A | 5/1987 | Roland et al. | |
| 4,704,116 A | 11/1987 | Enloe | |
| 4,739,910 A | 4/1988 | Westphal et al. | |
| 4,938,739 A * | 7/1990 | Nilsson | 493/422 |
| 4,938,757 A | 7/1990 | Van Gompel et al. | |
| 4,940,464 A | 7/1990 | Van Gompel et al. | |
| 5,040,783 A | 8/1991 | Ruehl | |
| 5,046,272 A | 9/1991 | Vogt et al. | |
| 5,104,116 A | 4/1992 | Pohjola | |
| 5,224,405 A | 7/1993 | Pohjola | |
| 5,226,992 A | 7/1993 | Morman | |
| 5,300,007 A | 4/1994 | Kober | |
| 5,492,591 A | 2/1996 | Herrmann et al. | |
| 5,537,806 A | 7/1996 | Grierson et al. | |
| 5,714,027 A | 2/1998 | Taub | |
| 5,788,805 A | 8/1998 | Herrmann | |
| 5,855,574 A | 1/1999 | Kling et al. | |
| 5,897,291 A | 4/1999 | Gerwe et al. | |
| 5,897,292 A | 4/1999 | Gerwe et al. | |
| 5,904,802 A | 5/1999 | Niedermeyer | |
| 6,017,406 A | 1/2000 | Vogt | |
| 6,036,805 A | 3/2000 | McNichols | |
| 6,079,562 A | 6/2000 | Bauer et al. | |
| 6,139,004 A | 10/2000 | Couillard et al. | |
| 6,250,357 B1 | 6/2001 | Niedermeyer | |
| 6,254,523 B1 * | 7/2001 | Yamamoto et al. | 493/451 |
| 6,254,714 B1 | 7/2001 | Niedermeyer | |
| 6,287,287 B1 | 9/2001 | Elsberg | |
| 6,461,344 B1 | 10/2002 | Widlund et al. | |
| 2003/0062113 A1 | 4/2003 | Van Eperen et al. | |
| 2003/0062120 A1 | 4/2003 | Lehner et al. | |

FOREIGN PATENT DOCUMENTS

| | | |
|---|---|---|
| EP | 0 217 032 | 2/1992 |
| EP | 0 631 766 A1 | 1/1995 |
| FR | 2 209 368 | 6/1974 |
| FR | 2 219 636 | 9/1974 |
| GB | 2 245 149 | 1/1992 |
| JP | 09131364 | 5/1997 |
| WO | WO 00/35398 | 6/2000 |
| WO | WO 00/37009 | 6/2000 |

* cited by examiner

METHOD OF TUCKING SIDE PANELS WITH SIDE PANEL FOLD LOCATION CONTROL

CROSS-REFERENCE TO RELATED APPLICATION

This application is a divisional of patent application Ser. No. 09/967,024, filed on 28 Sep. 2001; now U.S. Pat. No. 6,723,035.

BACKGROUND OF THE INVENTION

This invention is directed to a method of tucking side panels into a main body of a pant-like garment while maintaining control over the side panel fold location.

Pant-like garments, such as disposable training pants, as well as adult incontinence wear, infant and children's diapers, and swimwear, are typically folded into a compact configuration prior to packaging. The folded configuration typically includes folding the garment in half such that a front waist edge is aligned with and adjacent a back waist edge. For an even tidier appearance, the side panels or side portions of the garment can be tucked in between a front panel and a back panel of the garment.

Certain automated processes exist in which the side panels are mechanically tucked into the garments along a conveyor prior to the garments reaching a stacking or accumulation device. In such processes, as the garment is being conveyed towards the stacker, mechanical blades rotate or travel with the product machine direction and push the side panels in from each side of the conveyor. The location of the mechanical blades is relied upon to control the location of the resulting folds. Alternatively, pneumatic forces, such as air bars are used to tuck the side panels. However, the location of the side panel folds is often inconsistent when such processes are used.

Some processes use vacuum to hold products on a conveyor, but the vacuum is applied effectively only at the center of the chassis, and at a moderate level, for example around 15 inches of water. Such use of a vacuum is not effective along the sides of the chassis.

Another drawback to using conventional side panel tucking methods is that the side panels are typically tucked completely inside the garment, thereby obscuring the consumer's view of the side panels prior to purchasing the garment. Pant-like garments, such as swimwear, are sometimes produced with side panels of a different color than the body portions of the garments to enhance the appearance of the garments, thus creating greater consumer appeal. When the side panels are tucked completely inside the garment, only the body portion of the garment is visible to the consumer.

There is a need or desire for a method of tucking side panels in which the location of the side panel folds can be controlled.

SUMMARY OF THE INVENTION

In response to the discussed difficulties and problems encountered in the prior art, a new method of tucking side panels has been discovered.

The present invention is directed to a method of tucking a pair of opposing side panels into a body portion of a pant-like garment in which the location of the side panel folds can be controlled. The method involves the steps of positioning the body portion of the pant-like garment between an upper conveyor having an upper vacuum zone and a lower conveyor having a lower vacuum zone. The opposing vacuum forces from the upper and lower vacuum zones pull apart a front region of the body portion from a back region of the body portion. With the body portion in an open position, the side panels are pushed into the body portion towards one another, thereby creating longitudinal folds in the garment along outer longitudinal edges of the upper and lower vacuum zones. Either a mechanical tucking device or else a pair of fluid streams can be used to push the side panels into the body portion.

The vacuum zones extend in the transverse direction, or cross machine direction, relative to the garment. The longitudinal edges of the vacuum zones determine the location of the side panel folds. The vacuum zone edge remains constant relative to the fold points of the panels, thus producing consistent side panel folds. The vacuum zone edge remains constant at least through the tucking of the side panels and may be shut off later. A zone of lower vacuum in the center of the vacuum zones can be used to maintain control of the garment as the garment moves down the conveyors, with higher vacuum zones along the edges of the vacuum zones. The higher vacuum zones should have about the same width as the desired final product width of the tucked garment. Alternatively, the center vacuum zone may be higher than the vacuum zones along the edges, depending on the material upon which the vacuum zones are intended to act.

The upper and lower vacuum zones can be the same width as the front and back regions of the body portion, thereby creating folds along the edges of the body portion. Alternatively, the upper and lower vacuum zones can be wider than the front and back regions of the body portion, thereby only partially tucking the side panels into the garment while part of the side panels remain visible along the edges of the garment. One benefit of partially tucking the side panels is that pant-like garments having side panels of a different color than the body portion can have the colors of both the side panels and the body portion made visible to consumers while in the package. As another alternative, the upper and lower vacuum zones can be narrower than the front and back regions of the body portion, thereby tucking in the side panels, as well as part of the body portion itself.

Once the side panels are tucked into the garment, the side panel folds can be held in place by reducing the gap between the upper and lower conveyors. After the side panel tucking, the garment may be transferred to a stacker where the folds can be held in place, for example using stacker fingers or other suitable means.

With the foregoing in mind, it is a feature and advantage of the invention to provide a method of tucking side panels in which the location of the side panel folds can be controlled and consistent.

DEFINITIONS

Figure 1:
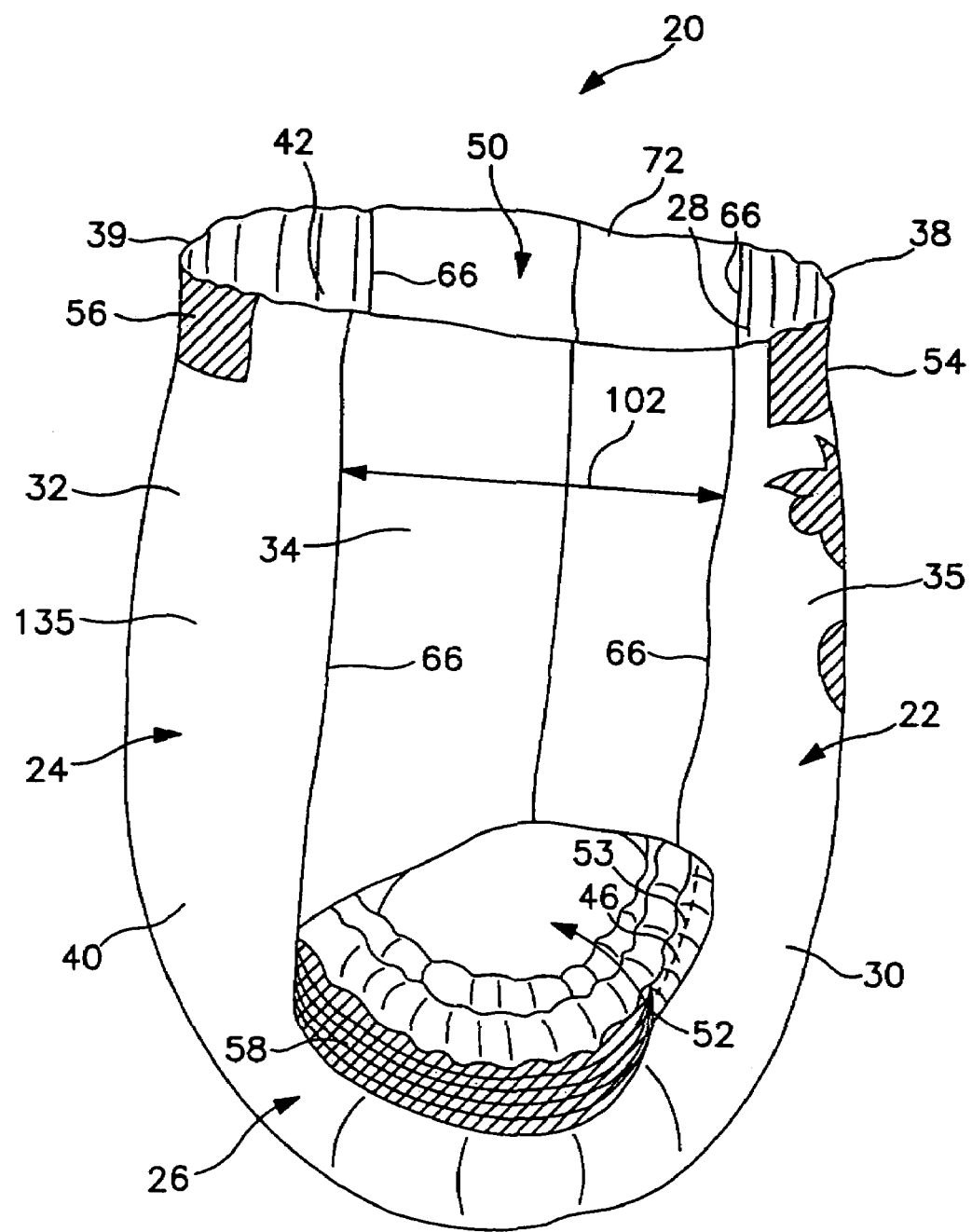
FIG. 1 is a perspective view of a training pant suitable for use in the present invention.

Within the context of this specification, each term or phrase below will include the following meaning or meanings.

"Attached" refers to the joining, adhering, connecting, bonding, or the like, of at least two elements. Two elements will be considered to be attached to one another when they are attached directly to one another or indirectly to one another, such as when each is directly connected to intermediate elements.

"Bonded" refers to the joining, adhering, connecting, attaching, or the like, of at least two elements. Two elements will be considered to be bonded together when they are bonded directly to one another or indirectly to one another, such as when each is directly bonded to intermediate elements.

"Elastomeric" and "elastic" refer to that property of a material or composite by virtue of which it tends to recover its original size and shape after removal of a force causing a deformation. It is generally preferred that the elastomeric material or composite be capable of being elongated by at least 50 percent, more preferably by at least 300 percent, of its relaxed length and recover, upon release of an applied force, at least 50 percent of its elongation.

"Film" refers to a thermoplastic film made using a film extrusion process, such as a cast film or blown film extrusion process. The term includes apertured films, slit films, and other porous films which constitute liquid transfer films, as well as films which do not transfer liquid.

"Layer" when used in the singular can have the dual meaning of a single element or a plurality of elements.

"Liquid impermeable," when used in describing a layer or laminate, means that liquid such as urine will not pass through the layer or laminate under ordinary use conditions in a direction generally perpendicular to the plane of the layer or laminate at the point of liquid contact.

"Liquid permeable material" or "liquid water-permeable material" refers to a layer or laminate that is not liquid impermeable.

"Longitudinal" and "transverse" have their customary meaning, as indicated by the longitudinal and transverse axes depicted in FIGS. 2-5. The longitudinal axis lies in the plane of the article and is generally parallel to a vertical plane that bisects a standing wearer into left and right body halves when the article is worn. The transverse axis lies in the plane of the article generally perpendicular to the longitudinal axis.

"Meltblown fiber" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 0.6 denier, and are generally self bonding when deposited onto a collecting surface. Meltblown fibers used in the present invention are preferably substantially continuous in length.

"Member" when used in the singular can have the dual meaning of a single element or a plurality of elements.

"Nonwoven" and "nonwoven web" refer to materials and webs of material which are formed without the aid of a textile weaving or knitting process.

"Operatively joined," in reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

"Polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

"Spunbonded fiber" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average deniers larger than about 0.3, more particularly, between about 0.6 and 10.

"Stretchable" means that a material can be stretched, without breaking, to at least 150% of its initial (unstretched) length in at least one direction, suitably to at least 250% of its initial length, desirably to at least 300% of its initial length.

"Superabsorbent" or "superabsorbent material" refers to a water-swellable, water-insoluble organic or inorganic material capable, under the most favorable conditions, of absorbing at least about 15 times its weight and, more desirably, at least about 30 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers.

"Surface" includes any layer, film, woven, nonwoven, laminate, composite, or the like, whether pervious or impervious to air, gas, and/or liquids.

"Tucked" refers to a folded state of a garment in which at least one portion of the garment is inserted into the body portion to create a more compact orientation of the garment.

These terms may be defined with additional language in the remaining portions of the specification.

DETAILED DESCRIPTION OF THE PRESENTLY PREFERRED EMBODIMENTS

The present invention is directed to a method of tucking a pair of side panels into a body portion of a pant-like garment. The method allows the location of the side panel folds to be controlled. A detailed description of the tucking process follows a description of the garment below.

The principles of the present invention can be used with any suitable pant-like garment, such as training pants, swim pants, diapers, incontinence products, other personal care or health care garments, including medical garments, or the like. As used herein, the term "incontinence products" includes absorbent underwear for children, absorbent garments for children or young adults with special needs such as autistic children or others with bladder/bowel control problems as a result of physical disabilities, as well as absorbent garments for incontinent older adults. For ease of explanation, the description hereafter will be in terms of a child's training pant.

Referring to FIG. 1, a training pant 20 is illustrated. The training pant 20 includes a pair of side panels 34, each extending from a waist opening 50 to one of two leg openings 52 on opposing sides of the pant 20. The side panels 34 can either be integrally formed with a body portion 32 of the pant 20, or can each include at least one separate element permanently attached to the body portion 32, as shown in FIG. 1.

The body portion 32 defines a front region 22, a back region 24, a crotch region 26 interconnecting the front and back regions, an inner surface 28 which is configured to contact the wearer, and an outer surface 30 opposite the inner surface which is configured to contact the wearer's clothing. The body portion 32 also defines a pair of longitudinally opposed waist edges, which are designated front waist edge 38 and back waist edge 39. The front region 22 is contiguous with the front waist edge 38, and the back region 24 is contiguous with the back waist edge 39.

In the training pant 20 illustrated in FIG. 1, the front and back regions 22 and 24 are joined together to define a three-dimensional pant configuration having a waist opening 50 and a pair of leg openings 52. The front region 22 includes the portion of the training pant 20 which, when worn, is positioned on the front of the wearer while the back region 24 includes the portion of the training pant which, when worn, is positioned on the back of the wearer. The crotch region 26 of the training pant 20 includes the portion of the training pant which, when worn, is positioned between the legs of the wearer and covers the lower torso of the wearer.

The front region 22 of the body portion 32 includes a front panel 35 positioned between and interconnecting the side panels 34, along with a front waist elastic member 54 and any other connected components. The back region 24 of the body portion 32 includes a back panel 135 positioned between and interconnecting the side panels 34, as well as a rear waist elastic member 56 and any other connected components.

The body portion 32 is configured to contain and/or absorb any body exudates discharged from the wearer. For example, the body portion 32 desirably, although not necessarily, includes a pair of containment flaps 46 which are configured to provide a barrier to the transverse flow of body exudates. A flap elastic member 53 can be operatively joined with each containment flap 46 in any suitable manner as is well known in the art. The elasticized containment flaps 46 define an unattached edge which assumes an upright, generally perpendicular configuration in at least the crotch region 26 of the training pant 20 to form a seal against the wearer's body. The containment flaps 46 can extend longitudinally along the entire length of the body portion 32 or may only extend partially along the length of the body portion. Suitable constructions and arrangements for the containment flaps 46 are generally well known to those skilled in the art and are described in U.S. Pat. No. 4,704,116 issued Nov. 3, 1987 to Enloe, which is incorporated herein by reference.

The illustrated body portion 32 can include an outer cover 40, a bodyside liner 42 which is connected to the outer cover in a superposed relation, and an absorbent assembly (not shown) which is located between the outer cover 40 and the bodyside liner 42.

To further enhance containment and/or absorption of body exudates, the training pant 20 can include the front waist elastic member 54, the rear waist elastic member 56, and leg elastic members 58, as are known to those skilled in the art. The waist elastic members 54 and 56 can be operatively joined to the outer cover 40 and/or bodyside liner 42 along the opposite waist edges 38 and 39 as well as over waist edges 72 of the side panels 34, and can extend over part or all of the waist edges. The leg elastic members 58 can be operatively joined to the outer cover 40 and/or bodyside liner 42 while longitudinally aligned along the distal edges and positioned in the crotch region 26 of the body portion 32.

The flap elastic members 53, the waist elastic members 54 and 56, and the leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the leg elastic members 58 include a plurality of dry-spun coalesced multifilament spandex elastomeric threads sold under the trade name LYCRA® and available from E.I. DuPont de Nemours and Company, Wilmington, Del., U.S.A.

The outer cover 40 desirably includes a material that is substantially liquid impermeable, and can be elastic, stretchable or nonstretchable. The outer cover 40 can be a single layer of liquid impermeable material, but desirably includes a multi-layered laminate structure in which at least one of the layers is liquid impermeable. For instance, the outer cover 40 can include a liquid permeable outer layer and a liquid impermeable inner layer that are suitably joined together thermally, ultrasonically, by a laminate adhesive, or by any other suitable methods known in the art. Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J., U.S.A. The liquid permeable outer layer can be any suitable material and desirably one that provides a generally cloth-like texture and/or mating fastening component qualities. One example of such a material is a 20 gsm (grams per square meter) spunbond polypropylene nonwoven web. The outer layer may also be made of those materials of which liquid permeable bodyside liner 42 is made. While it is not a necessity for the outer layer to be liquid permeable, it is desired that it provides a relatively cloth-like texture to the wearer.

The inner layer of the outer cover 40 can be both liquid and vapor impermeable, or can be liquid impermeable and vapor permeable. The inner layer is desirably manufactured from a thin plastic film, although other flexible liquid impermeable materials may also be used. The inner layer, or the liquid impermeable outer cover 40 when a single layer, prevents waste material from wetting articles, such as bedsheets and clothing, as well as the wearer and care giver. A suitable liquid impermeable film for use as a liquid impermeable inner layer, or a single layer liquid impermeable outer cover 40, is a 0.2 millimeter polyethylene film commercially available from Huntsman Packaging of Newport News, Va., U.S.A. If the outer cover 40 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 40. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn.

The liquid permeable bodyside liner 42 may but need not have the same dimensions as the outer cover 40. The bodyside liner 42 is desirably compliant, soft feeling, and non-irritating to the child's skin. Further, the bodyside liner 42 can be less hydrophilic than the absorbent assembly, to present a relatively dry surface to the wearer and permit liquid to readily penetrate through its thickness.

The bodyside liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 42. For example, the bodyside liner can be composed of a meltblown or spunbonded web of polyolefin fibers. The bodyside liner can also be a bonded-carded web composed of natural and/or synthetic fibers. The bodyside liner can be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture including AHCOVEL® N-62 from Uniqema, Inc., a division of ICI of New Castle, Del., and GLUCOPON® 220UP from Cognis Corp. of Ambler, Pa., in an active ratio of 3:1. The surfactant can be applied by any conventional means, such as spraying, printing, brush coating or the like. The surfactant can be applied to the entire bodyside liner 42 or can be selectively applied to particular sections of the bodyside liner, such as the medial section along the longitudinal centerline.

A suitable liquid permeable bodyside liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like. While the outer cover 40 and bodyside liner 42 can include elastomeric materials, it can be desirable in some embodiments for the composite structure to be generally inelastic, where the outer cover, the bodyside liner and the absorbent assembly include materials that are generally not elastomeric.

The absorbent assembly (not shown) is positioned between the outer cover 40 and the bodyside liner 42, which components can be joined together by any suitable means, such as adhesives, as is well known in the art. The absorbent assembly can be any structure which is generally compressible, conformable, non-irritating to the child's skin, and capable of absorbing and retaining liquids and certain body wastes. The absorbent assembly can be manufactured in a wide variety of sizes and shapes, and from a wide variety of liquid absorbent materials commonly used in the art. For example, the absorbent assembly can suitably include a matrix of hydrophilic fibers, such as a web of cellulosic fluff, mixed with particles of a high-absorbency material commonly known as superabsorbent material. High absorbency material can be provided in any form known in the art, including but not limited to particles, fibers, foams and films.

In a particular embodiment, the absorbent assembly includes a matrix of cellulosic fluff, such as wood pulp fluff, and superabsorbent hydrogel-forming particles. The wood pulp fluff can be exchanged with synthetic, polymeric, meltblown fibers or with a combination of meltblown fibers and natural fibers. The superabsorbent particles can be substantially homogeneously mixed with the hydrophilic fibers or can be nonuniformly mixed. The fluff and superabsorbent particles can also be selectively placed into desired zones of the absorbent assembly to better contain and absorb body exudates. The concentration of the superabsorbent particles can also vary through the thickness of the absorbent assembly. Alternatively, the absorbent assembly can include a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent assembly is generally rectangular in shape, and includes a blend of wood pulp fluff and superabsorbent material. One preferred type of fluff is identified with the trade designation CR1654, available from U.S. Alliance, Childersburg, Ala., U.S.A., and is a bleached, highly absorbent sulfate wood pulp containing primarily soft wood fibers. As a general rule, the superabsorbent material is present in the absorbent assembly in an amount of from about >0 to about 90 weight percent based on total weight of the absorbent assembly. The absorbent assembly suitably has a density within the range of about 0.10 to about 0.50 grams per cubic centimeter. The absorbent assembly may or may not be wrapped or encompassed by a suitable tissue wrap that maintains the integrity and/or shape of the absorbent assembly.

The body portion 32 can also incorporate other materials that are designed primarily to receive, temporarily store, and/or transport liquid along the mutually facing surface with the absorbent assembly, thereby maximizing the absorbent capacity of the absorbent assembly. One suitable material is referred to as a surge layer (not shown) and includes a material having a basis weight of about 50 to about 120 grams per square meter, and including a through-air-bonded-carded web of a homogenous blend of 60 percent 3 denier type T-256 bicomponent fiber including a polyester core/polyethylene sheath and 40 percent 6 denier type T-295 polyester fiber, both commercially available from Kosa Corporation of Salisbury, N.C., U.S.A.

As noted previously, the side panels 34 are disposed on each side of the body portion 32, and may each include one or more pieces of material. These transversely opposed side panels 34 can be permanently bonded to the front panel 35 and back panel 135 in the respective front and back regions 22, 24 along attachment lines 66, using attachment means known to those skilled in the art such as adhesive, thermal or ultrasonic bonding. As mentioned, the side panels 34 can also be formed as continuous extensions of the front and back panels 35, 135.

In particular embodiments for improved fit and appearance, the side panels 34 desirably have an average length dimension measured parallel to the longitudinal axis 48 that is about 20 percent or greater, and particularly about 25 percent or greater, of the overall length dimension of the absorbent article, also measured parallel to the longitudinal axis 48. For example, in training pants 20 having an overall length dimension of about 54 centimeters, the side panels 34 desirably have an average length dimension of about 10 centimeters or greater, such as about 15 centimeters. The longitudinal axis 48 and transverse axis 49 are shown in FIGS. 2-5.

The side panels 34 desirably include an elastic material capable of stretching in a direction generally parallel to the transverse axis 49 of the training pant 20. Suitable elastic materials, as well as one described process of incorporating elastic side panels into a training pant, are described in the following U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular embodiments, the elastic material includes a stretch-thermal laminate (STL), a neck-bonded laminated (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; and European Patent Application No. EP 0 217 032 published on Apr. 8, 1987 in the names of Taylor et al.; all of which are incorporated herein by reference. Alternatively, the side panel material may include other woven or nonwoven materials, such as those described above as being suitable for the outer cover 40 or bodyside liner 42, or stretchable but inelastic materials.

Figure 2:
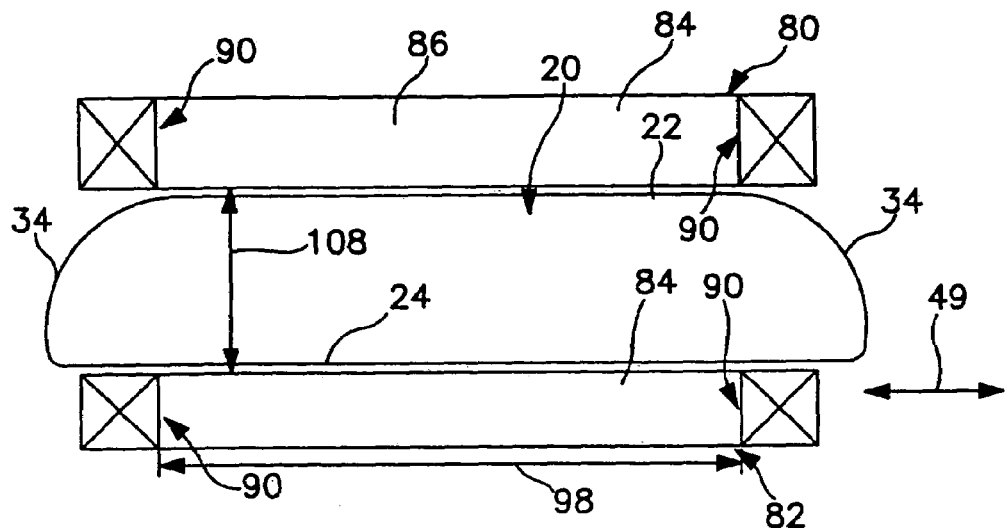
FIG. 2 is an end view of a training pant between upper and lower vacuum conveyors.

In carrying out the method of the invention, the training pant 20 is suitably substantially assembled with the side panels 34 bonded, as shown in FIG. 1. The training pant 20 is placed between an upper vacuum conveyor 80 and a lower vacuum conveyor 82, as shown in FIG. 2, with either the front region 22 facing up or the back region 24 facing up. As used herein, the term "conveyor" refers to either one conveyor or a series of conveyors acting in cooperation with one another. Vacuum portions 84 within the upper and lower conveyors 80, 82 pull the front region 22 and the back region 24 of the garment 20 apart from one another.

In another embodiment, only one of the conveyors 80, 82 has a vacuum portion 84. One conveyor, either an upper conveyor 80 or a lower conveyor 82, with a vacuum portion 84 may be sufficient to hold the training pant 20 in place during the method of the invention.

Figure 3:
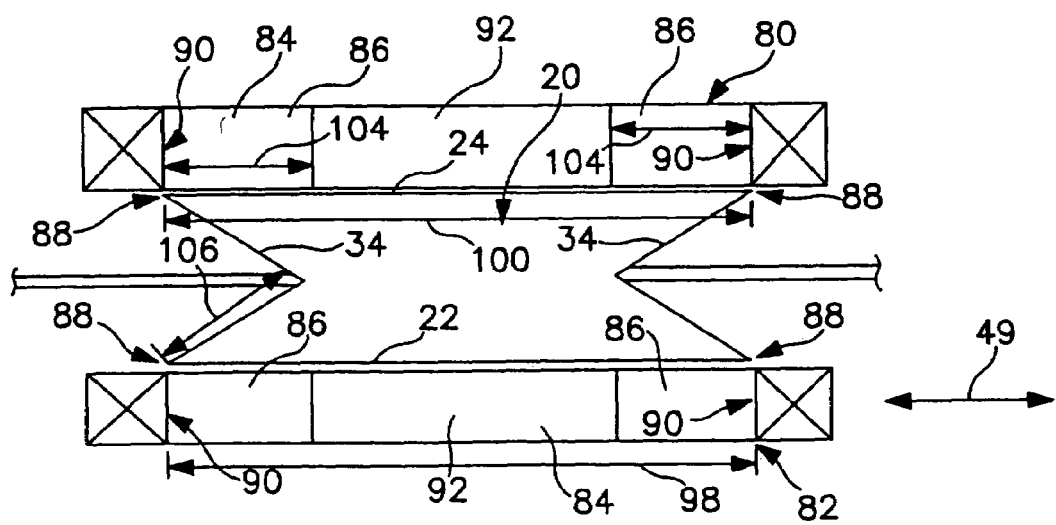
FIG. 3 is an end view of a training pant between upper and lower vacuum conveyors with side panels being tucked into the training pant.

The vacuum portions 84 can each include either one high vacuum zone 86 that extends in the cross machine, or transverse, direction 49 from one longitudinal side panel fold 88 to another longitudinal side panel fold 88, as shown in FIG. 2, or two high vacuum zones 86 along outer longitudinal edges 90 of the vacuum portion 84 with a lower vacuum zone 92 situated between the two high vacuum zones 86, as shown in FIG. 3. In the embodiment having multiple vacuum zones 86, the vacuum zones 86 need not be abutted against one another but may have non-vacuum, or dead air, zones between the vacuum zones 86. The lower vacuum zone 92 can be used to maintain control of the training pant 20 as the training pant moves down the conveyors 80, 82. Alternatively, the two vacuum zones along the outer longitudinal edges 90 of the vacuum portion 84 may have a lower vacuum than the vacuum zone situated between the two vacuum zones. The relative strength of the vacuum zones should be commensurate with the fabric to be handled by the respective zones. For instance, materials that are less permeable would be expected to require less vacuum to hold them firmly in place.

The high vacuum zones 86 must be strong enough to maintain the training pant 20 in the open position with the front region 22 pulled apart from the back region 24. In order to do so, the vacuum is suitably maintained in a range of about 0 to about 100 inches of water. At relatively high speed, a vacuum of at least 25 inches of water is desirable. In one embodiment of the invention, the high vacuum zones 86 can be shifted to the right or left of the machine centerline to adapt for any weave that may be present in the product path. Furthermore, the width of the high vacuum zones 86 can be adjusted, for example using dead plates, to adapt for different product sizes.

Figure 4:
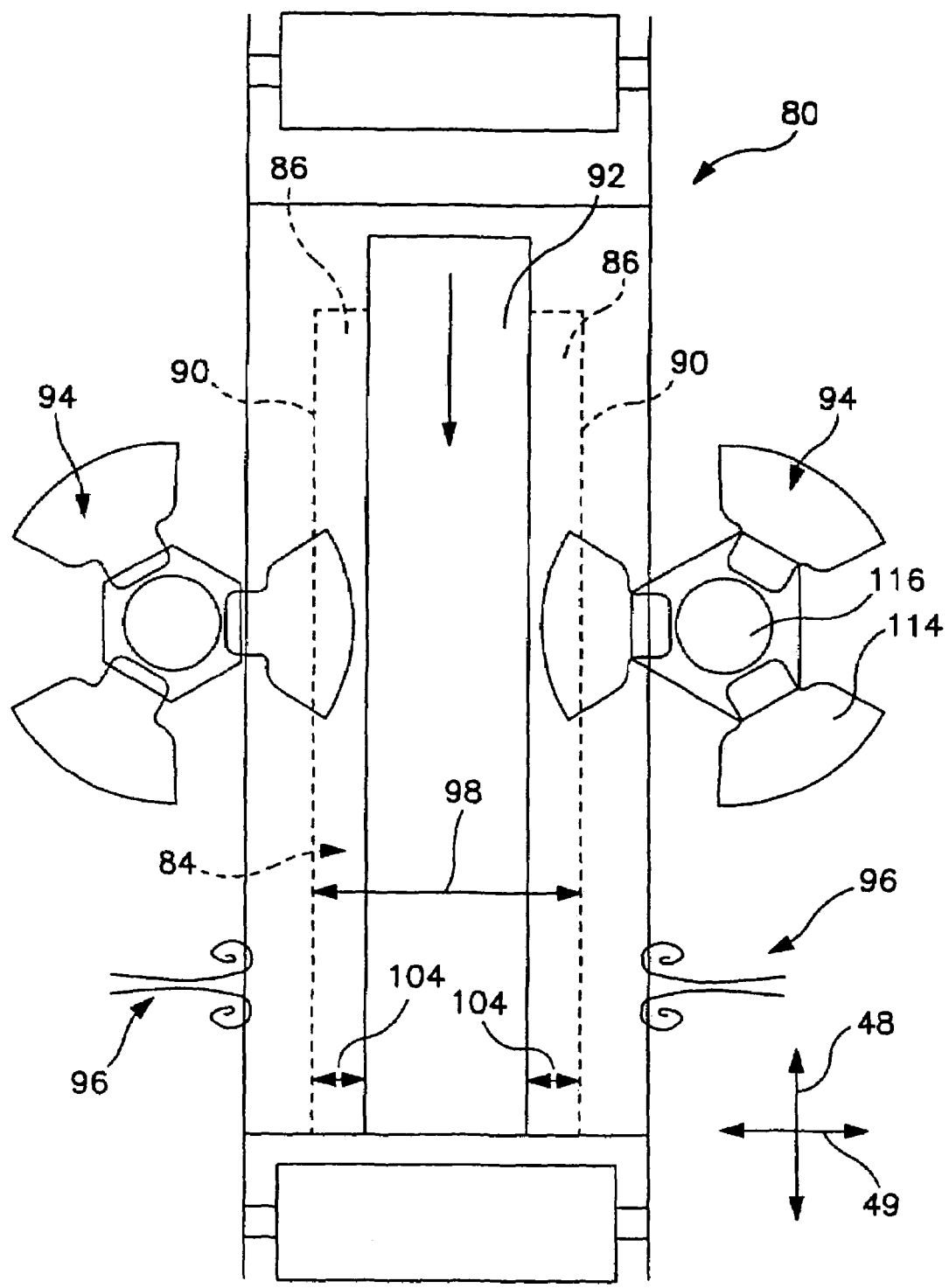
FIG. 4 is a top view of a conveyor in a dual conveyor apparatus.

Once the pant 20 is open, the side panels 34 can be tucked, or at least partially tucked, into the body portion 32 of the pant, as shown in FIGS. 3 and 4, either by using a mechanical tucking device 94 or by using fluid streams 96, such as air blasts or a vacuum, directed toward the side panels 34 to push the side panels 34 inward a certain distance 106 toward one another. The mechanical tucking device 94 and/or pneumatic air pressure 96 are used to push the side panels 34 into the training pant 20 such that the longitudinal folds 88 are at the edges 90 of the high vacuum portion 84, as shown in FIG. 3.

Figure 5:
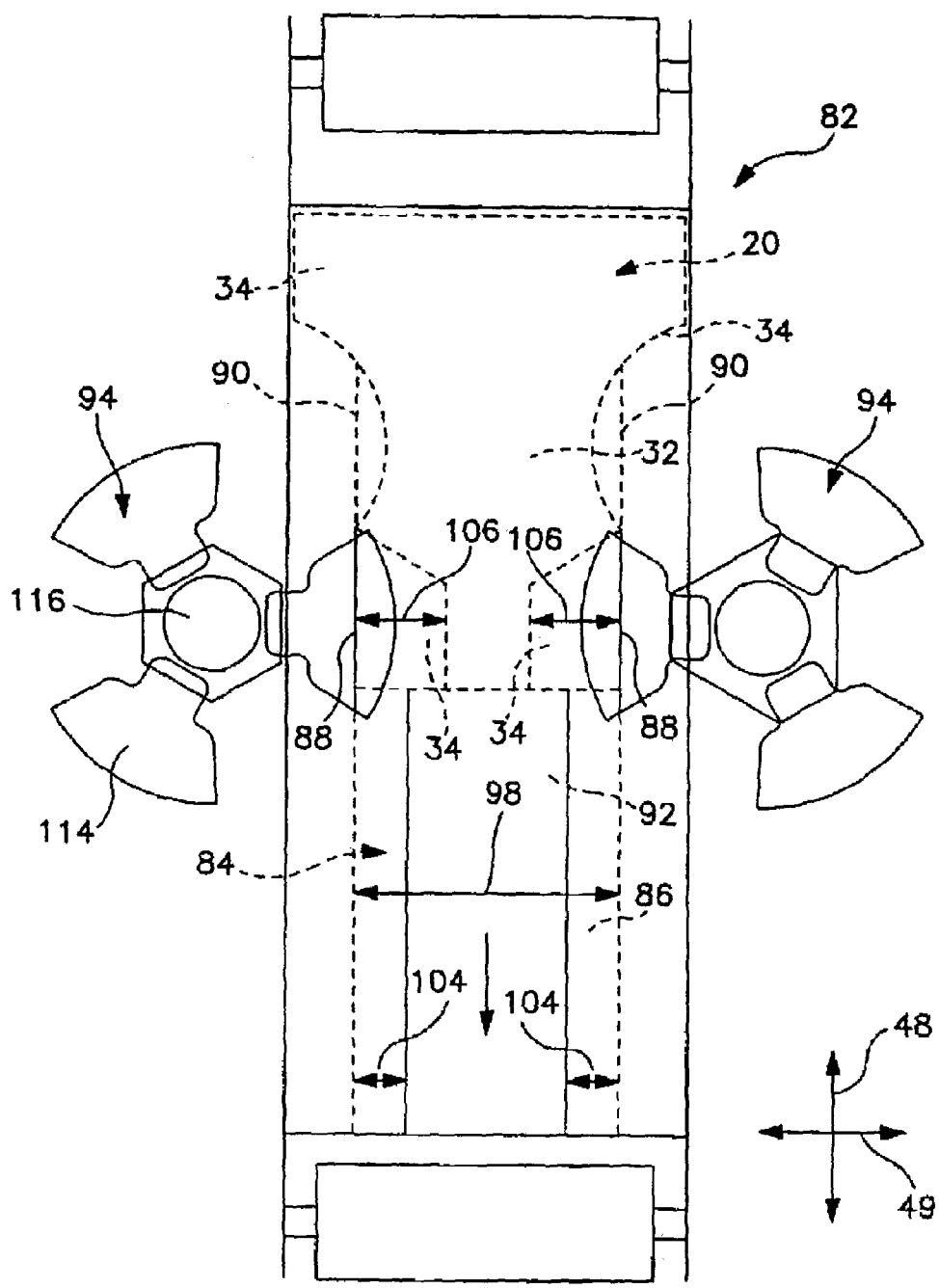
FIG. 5 is a top view of a conveyor in a single conveyor apparatus.

In another embodiment of the invention, the garment 20 is an open product, such as a diaper, without bonded side panels and the method of the invention is used to fold the side panels 34 onto the body portion of the garment. An illustration of this embodiment is shown in FIG. 5. More particularly, the garment 20 can be placed on either an upper vacuum conveyor 80 or a lower vacuum conveyor 82, with the outer cover 40 of the garment 20 adjacent the conveyor. A vacuum portion 84 within either the upper or lower conveyor holds the body portion 32 against the conveyor. The side panels 34 can then be tucked, or at least partially tucked, over the body portion 32 of the pant either by using a mechanical tucking device 94 or by using fluid streams 96, such as air blasts, directed toward the side panels 34 to push the side panels 34 inward a certain distance 106 toward one another. As in the previous embodiment, the mechanical tucking device 94 and/or pneumatic air pressure 96 are used to push the side panels 34 onto the diaper 20 such that the longitudinal folds 88 are at the edges of the vacuum portion, as shown in FIG. 5.

Figure 6:
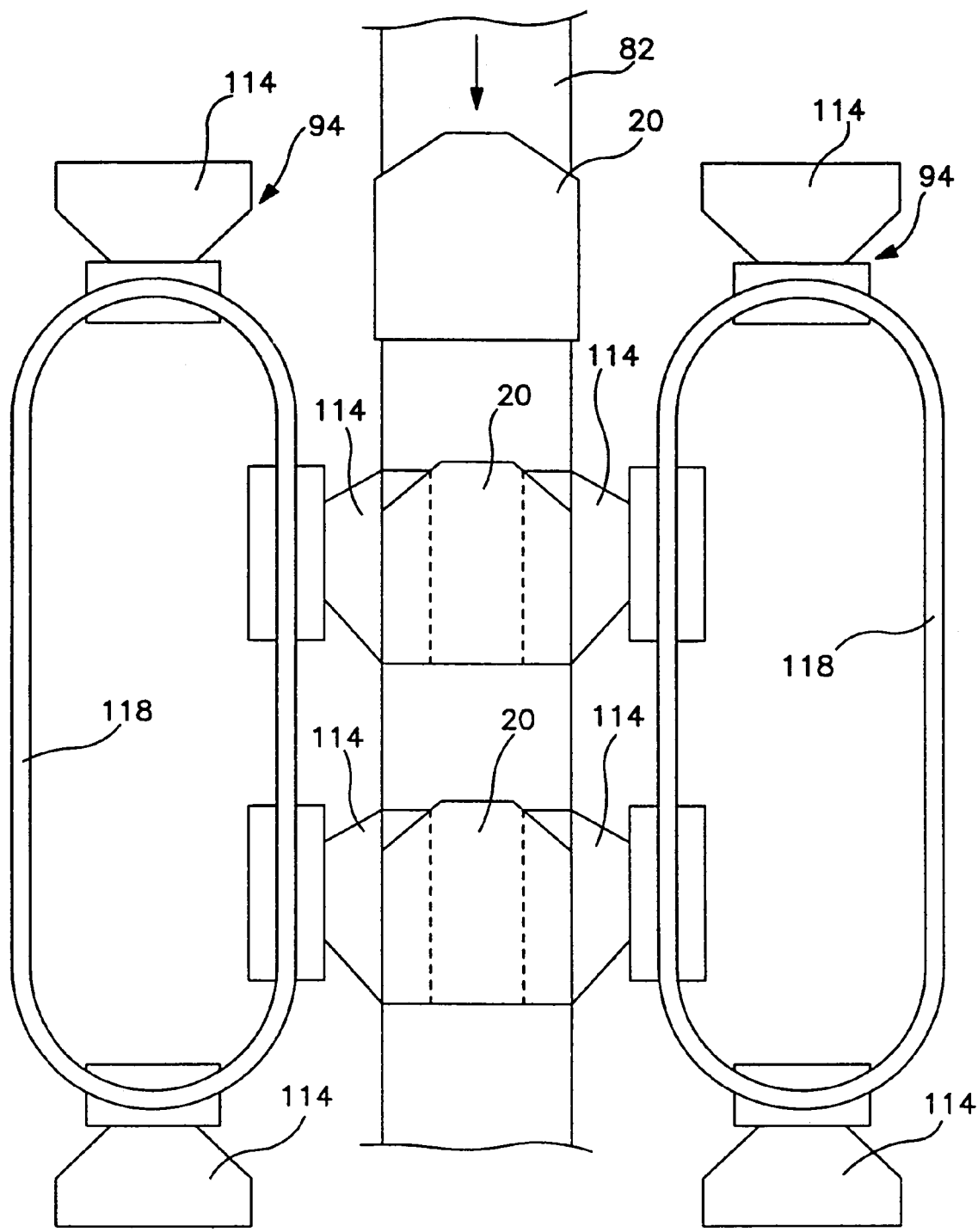
FIG. 6 is a top view of a conveyor between two tracks that guide mechanical tucking devices.
Figure 7:
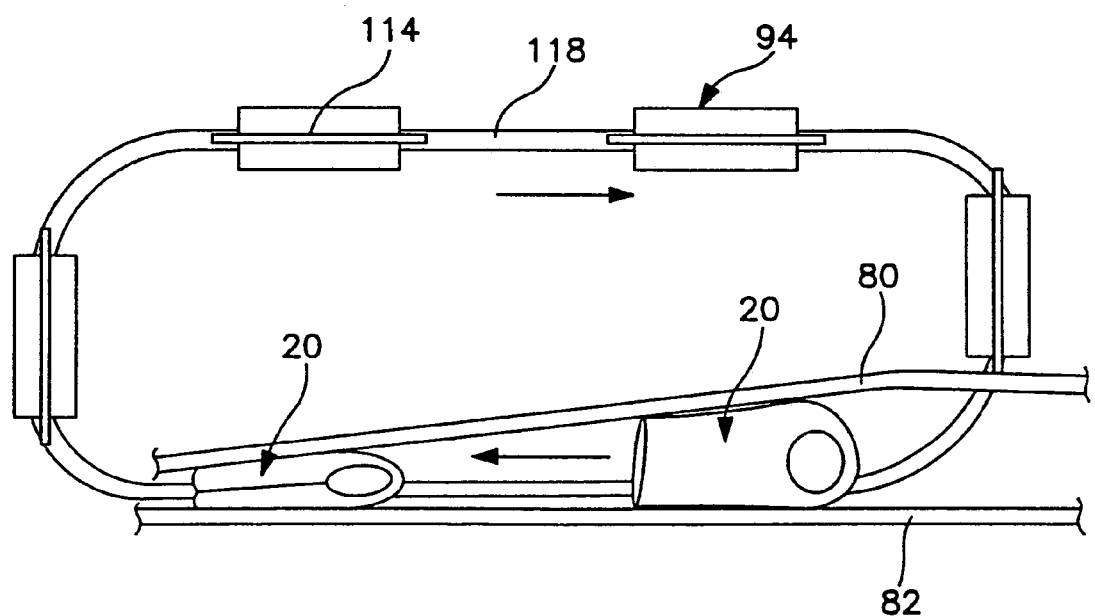
FIG. 7 is a side view of a track that guides mechanical tucking devices adjacent a conveyor.
Figure 8:
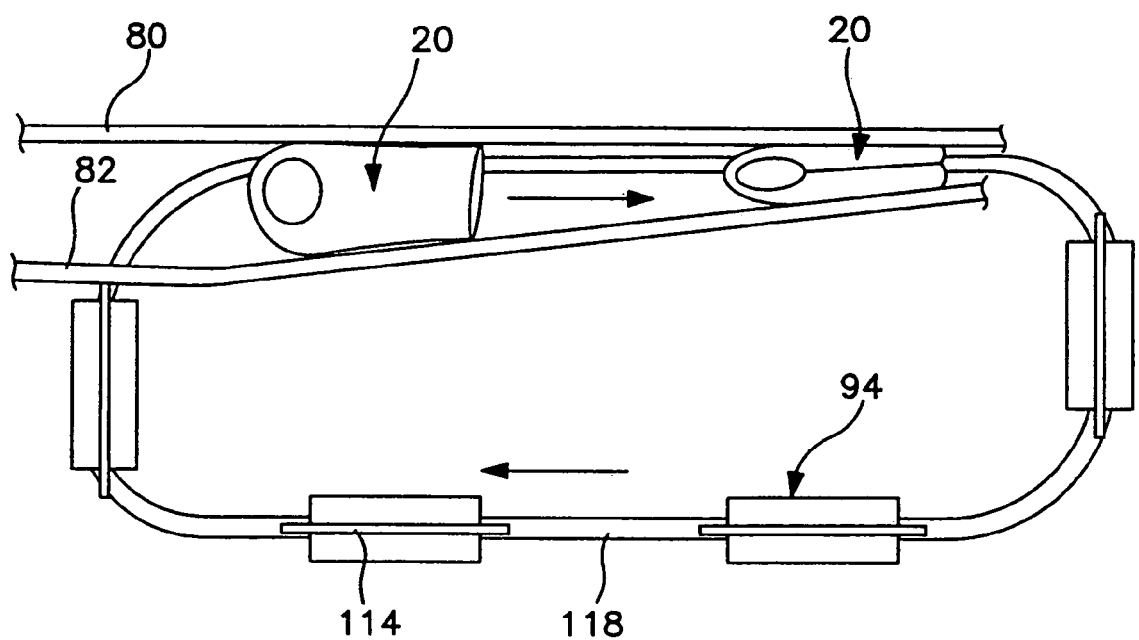
FIG. 8 is a side view of another track that guides mechanical tucking devices adjacent a conveyor.

Examples of suitable mechanical tucking devices 94 include mechanical tucking arms, or mechanical tucking blades 114 on a rotary paddle 116, as shown in FIGS. 4 and 5. In one embodiment, shown in FIGS. 6, 7, and 8, the path of a track 118 that guides the mechanical tucking device 94 can be designed so that the mechanical tucking device 94 travels with the pant 20 over a longer path length than with a rotary paddle. The mechanical tucking device 94 can be held essentially parallel to the track path 118 and travel generally in the plane of the folded pant 20, as shown in FIG. 6. As used herein, the term "essentially parallel" refers to mechanical tucking devices 94 that move either parallel to the track path 118 or mechanical tucking devices 94 that move parallel to the track path 118 for the most part but may move slightly toward the center of the pant 20 as the side panels 34 are tucked. Alternatively, the mechanical tucking device 94 can be held at an angle to the track path 118 and travel both in the plane of the folded pant 20 and above it, as shown in FIG. 7, or below it, as shown in FIG. 8. By using a track 118 designed in this manner, the mechanical tucking device 94 can match the speed of travel of the pant 20 for a longer time. For example, the speed of a tucking blade 114 in the machine direction depends on the point of rotation of the rotary paddle 116, with the speed being fastest when the tucking blade 114 is at closest approach to the pant 20. Also, because a tucking blade 114 on a track 118 can have full contact of its outer edge with the panel 34 of the pant, a straight-edge tucking blade 114 can be used.

A tucking blade 114 used in any mechanical tucking device 94 in the method of the invention can have an optimized shape so that a tail end of the tucking blades 114 does not knock the fold out of place. An example of an optimized shape is a circular blade 114 having cut-out portions, as shown in FIGS. 4 and 5. Also, different sizes and/or shapes of tucking blades 114 can be used for products of different sizes. A tucking blade 114 can also be shaped or adapted to provide unequal tucking of front versus back panels, or waist edge of the panel versus leg edge.

The fluid streams 96, or air blasts, when used to tuck or partially tuck the side panels 34, suitably exert a force commensurate with the material, or the porosity of the material, of which the side panels 34 are made. The force of the air blasts may also depend on the speed at which the process is running, and the machine direction length over which the air streams are applied. The fluid streams 96 may be air blasts directed toward an outer surface of the side panels 34, as shown in FIG. 4, or a vacuum at the center of the conveyor to draw the side panels inside the opened pant 20, or a combination of air blasts and vacuum.

Figure 9:
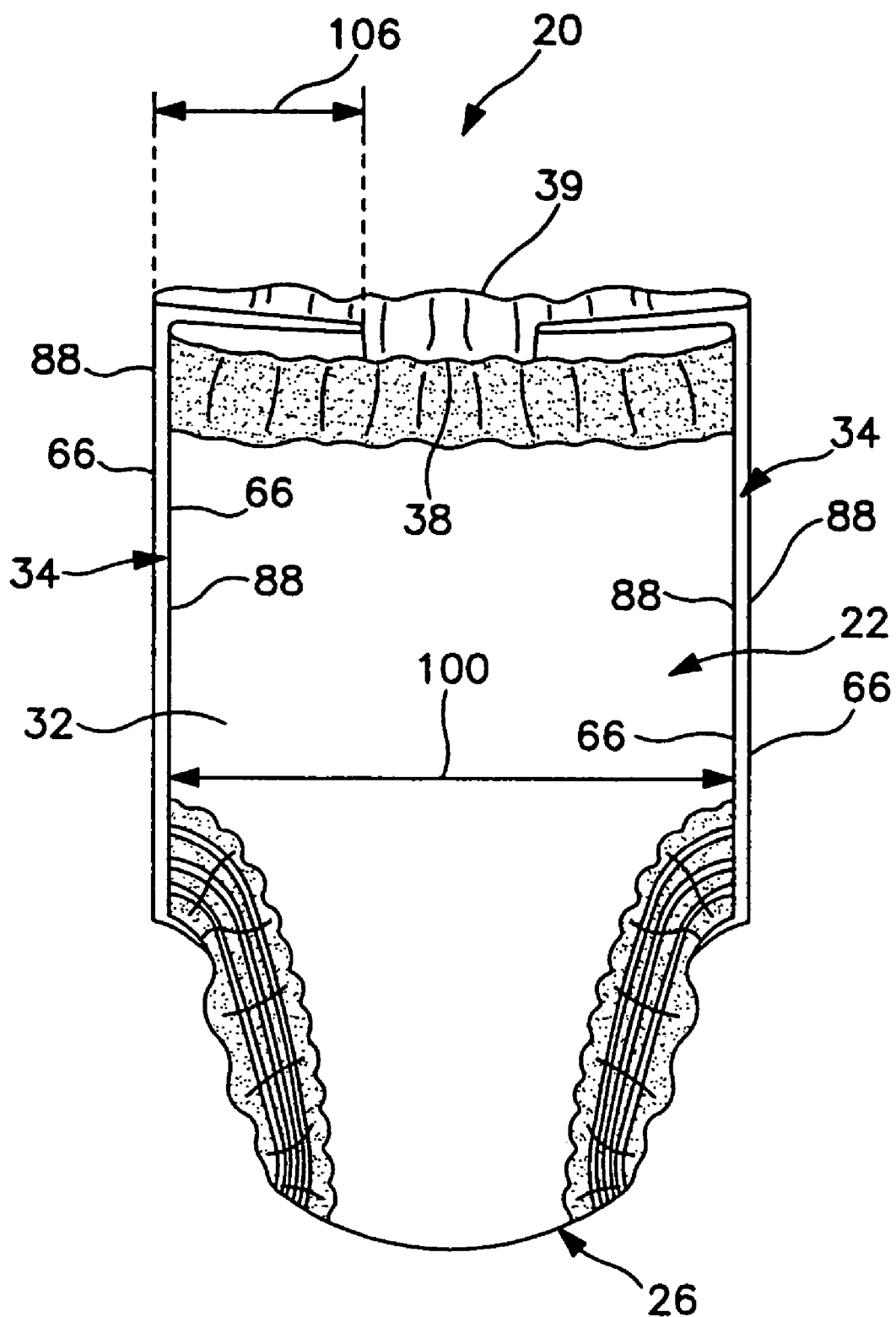
FIG. 9 is a perspective view of a training pant having longitudinal folds aligned along attachment lines between the side panels and the front and back regions.

The location of the longitudinal folds 88 is determined by the transverse width 98 of the vacuum portions 84 of the conveyors 80, 82. The longitudinal folds 88 occur at about the longitudinal edges 90 of the vacuum portions 84, as shown in FIG. 3. The widths 98 of the vacuum portions 84 can be approximately the same width as the width 100 of the front and back regions 22, 24 of the body portion 32, thereby placing the longitudinal folds 88 along the attachment lines 66 between the side panels 34 and the front and back panels 35, 135, as shown in FIG. 9. In this embodiment, the side panels 34 are pushed into the body portion 32 a distance approximately equal to one-half of a transverse width 102 of each of the pair of side panels 34, as shown in FIG. 1.

The training pant 20 can be aligned with the upper vacuum conveyor 80, the lower vacuum conveyor 82, and the mechanical tucking device 94 and/or fluid streams 96 such that the side panels 34 can be tucked with particular alignment of the side seam with respect to the apex of the tuck. For example, the side seam can be aligned with the apex of the tuck, or alternatively, the side seam can be aligned such that it is intentionally off the apex of the tuck.

Figure 10:
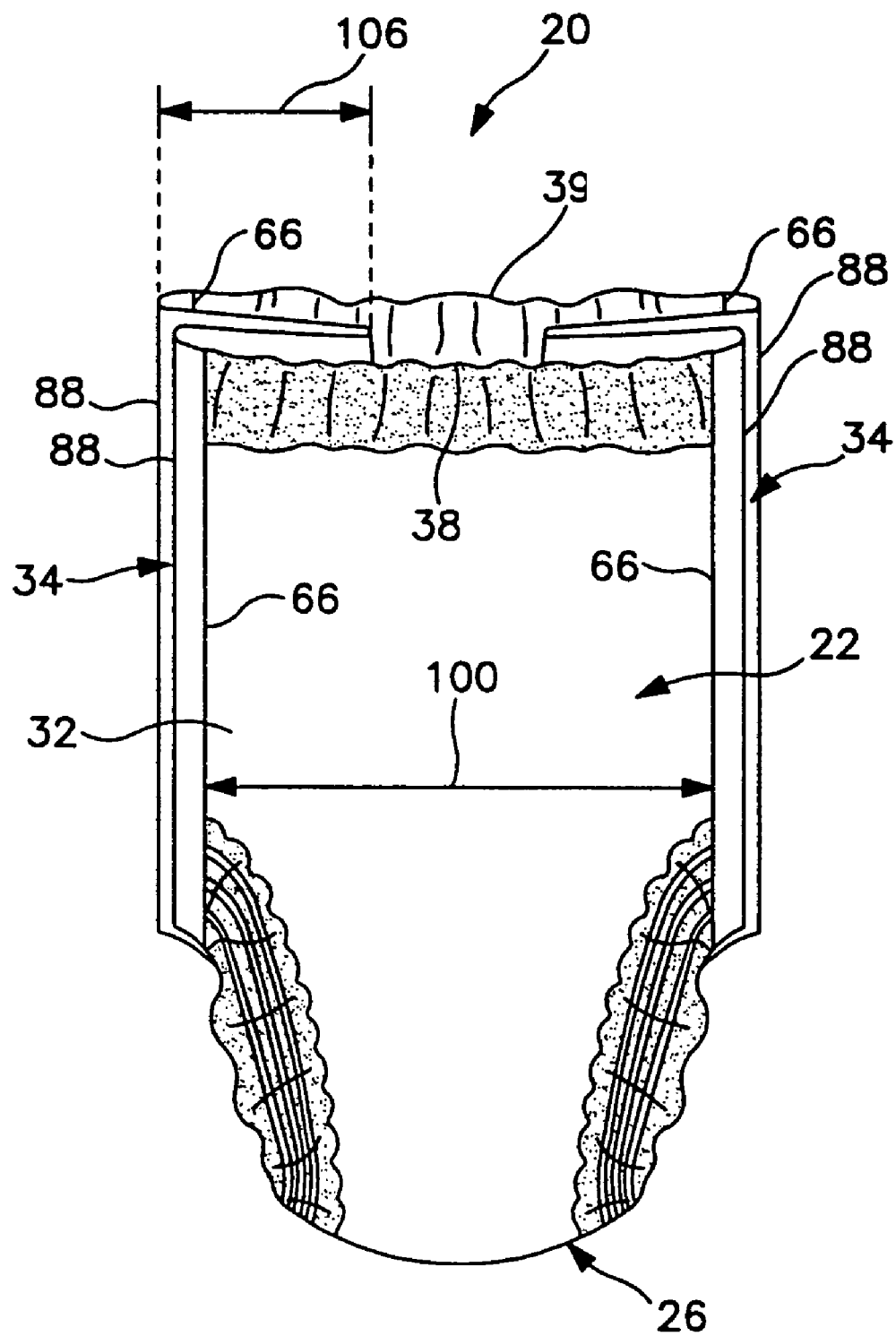
FIG. 10 is a perspective view of a training pant having longitudinal folds aligned along the side panels.

To partially tuck the side panels 34, the widths 98 of the vacuum portions 84 can be greater than the widths 100 of the front and back regions 22, 24 of the body portion 32, such that the longitudinal folds 88 occur on the side panels 34, thereby exposing edges of the side panels 34, as shown in FIG. 10. In this embodiment, the side panels 34 are pushed into the body portion 32 a distance 106 that is less than one-half of a transverse width 102 of each of the pair of side panels 34. This embodiment is particularly suitable for swimpants or other garments having side panels 34 of a color that is different than the color of the outer cover 40 of the body portion 32, since this embodiment displays both the side panel color and the outer cover color at the same time. This embodiment is also particularly suitable for side panels 34 that require some treatment after the tucking operation, such as heat activation of elastic material.

As another alternative, the transverse widths 98 of the vacuum portions 84 can be less than the widths 100 of the front and back regions 22, 24 of the body portion 32, such that the longitudinal folds 88 occur on the body portion 32 and edges of the body portion are tucked within the body portion. In any case, the vacuum portion transverse width 98 is approximately equal to the desired folded transverse width of the training pant 20. Furthermore, the transverse width 98 of the upper vacuum portion 84 may have a width equal to or different than the transverse width 98 of the lower vacuum portion 84, depending on the desired folded transverse widths 100 of the front and back regions 22, 24, which may be the same or different from one another. Since the transverse width 98 of the vacuum portions 84 remains constant, the locations of the longitudinal folds 88 are fairly consistent from product to product.

Referring back to the embodiment in which the vacuum portions 84 include high and low vacuum zones 86, 92, the high vacuum zones 86 suitably each have a transverse width 104 wide enough to control the folded edge 88, as shown in FIG. 3.

Figure 11:
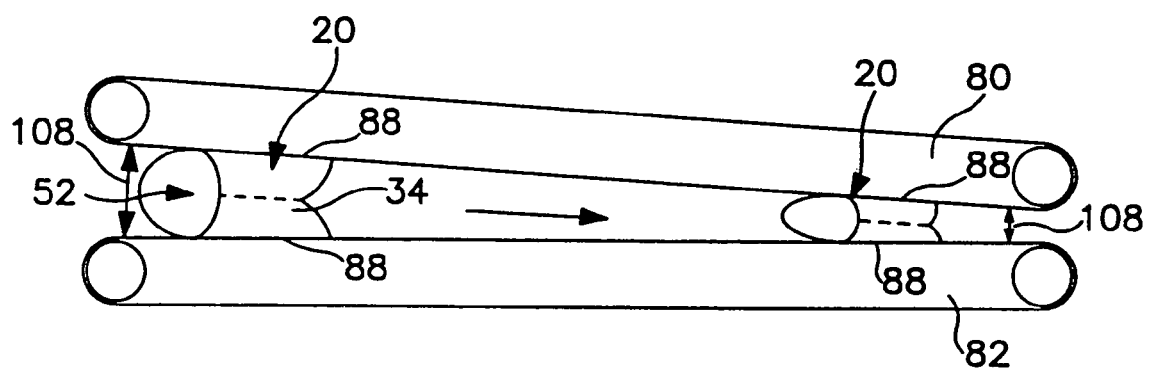
FIG. 11 is a side view of an arrangement of upper and lower vacuum conveyors.
Figure 12:
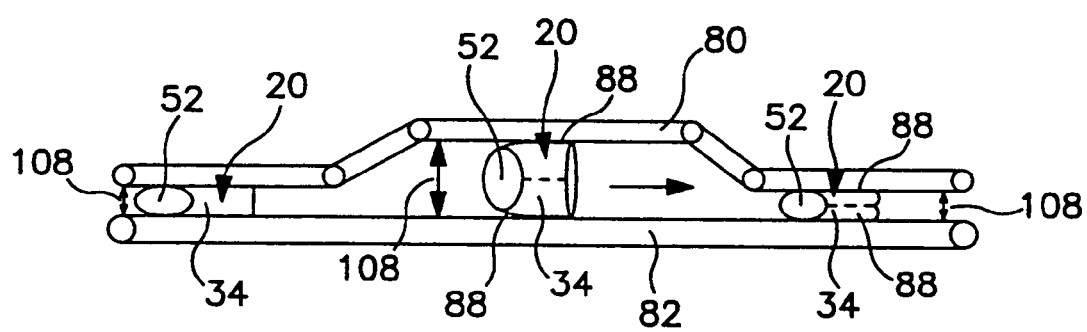
FIG. 12 is a side view of another arrangement of upper and lower vacuum conveyors.

Once the side panels 34 are tucked, or partially tucked, into the body portion 32, the longitudinal folds 88 may be held in place by reducing the distance 108 between the upper and lower conveyors 80, 82, as shown in FIG. 11. The upper and lower conveyors 80, 82 may converge either at the same time the side panels 34 are being tucked or after the side panels 34 have been tucked. Alternatively, the upper and lower conveyors 80, 82 may initially diverge, thereby increasing the distance 108 between the conveyors 80, 82 to permit panel tucking, then converge again, as shown in FIG. 12.

Figure 13:
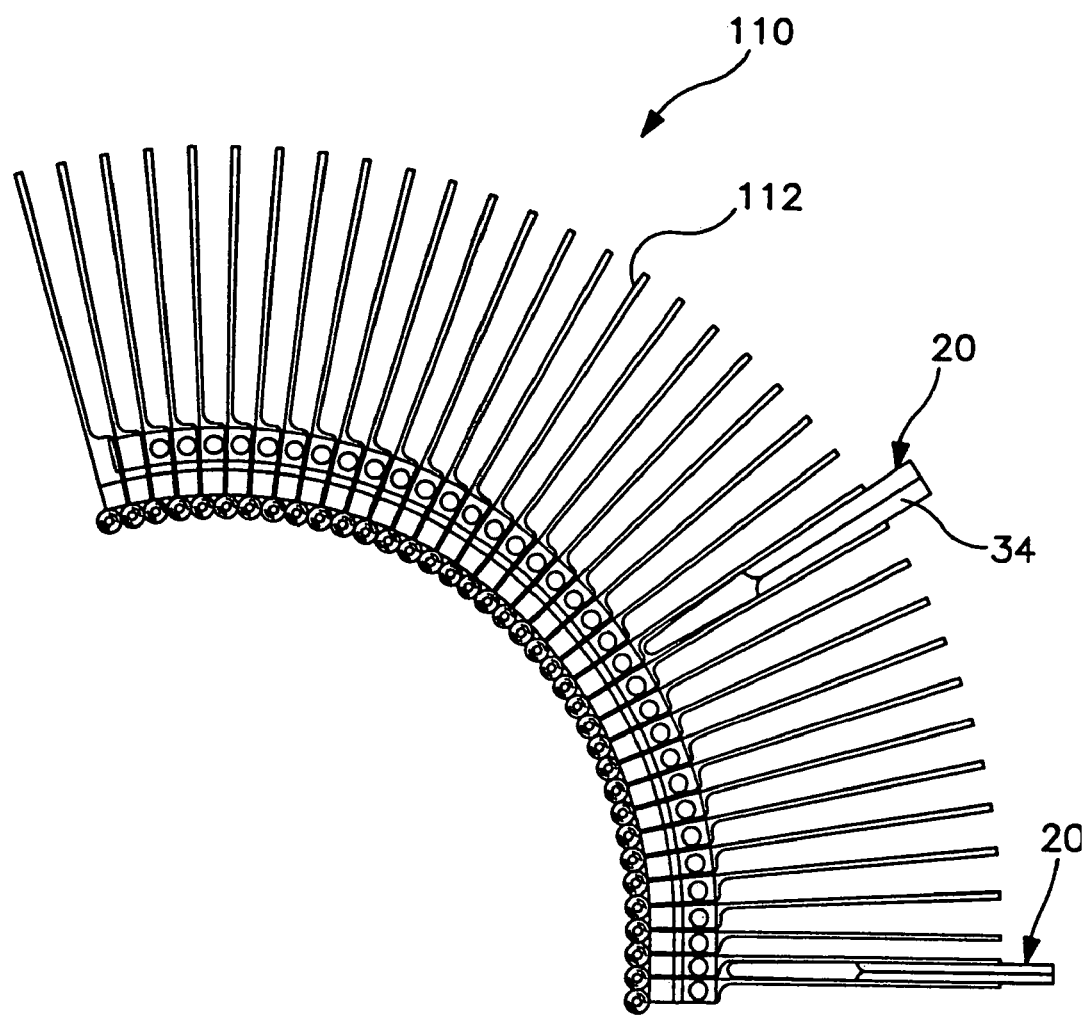
FIG. 13 is a plan view of driven stacker fingers.

The training pant 20 is then transferred to a stacker 110 or accumulation device, such as a portion of a driven stacker assembly 100 shown in FIG. 13, in which the longitudinal folds 88 are held in place by containment of the pant between consecutive stacker finger units 112. Consecutive stacker finger units 112 should be sufficiently spaced apart to maintain control of the folds 88 as the training pant 20 is transported through the driven stacker assembly 110.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

What is claimed is:

1. A method of tucking a pair of opposing side panels onto a body portion of a pant-like garment, comprising the steps of:
    positioning the body portion of the pant-like garment on a conveyor having a vacuum zone;
    holding the body portion on the conveyor using vacuum force from the vacuum zone; and
    using a mechanical tucking device to push the opposing side panels onto the body portion a distance toward one another while the vacuum force is holding the body portion on the conveyor, creating longitudinal folds in the garment along outer longitudinal edges of the vacuum zone, wherein the mechanical tucking device includes two opposing assemblies, each assembly including at least one tucking blade on a rotary paddle or at least one tucking blade conveyed along a track that guides the at least one tucking blade a distance alongside the conveyor.

2. The method of claim 1, wherein the vacuum zone comprises an outer area adjacent each of the outer longitudinal edges, the outer areas each having a first vacuum, and an inner area between the outer areas, the inner area having a second vacuum lower than the first vacuum.

3. The method of claim 1, wherein the vacuum zone comprises an outer area adjacent each of the outer longitudinal edges, the outer areas each having a first vacuum, and an inner area between the outer areas, the inner area having a second vacuum higher than the first vacuum.

4. The method of claim 1, wherein the vacuum zone comprises a uniform vacuum across a transverse width of the vacuum zone.

5. The method of claim 1, wherein the vacuum zone has a transverse width about equal to a desired folded transverse width of the body portion of the garment.

6. The method of claim 1, wherein the longitudinal folds are created in the body portion of the pant-like garment.

7. The method of claim 1, wherein the longitudinal folds are created along seams joining the side panels to the body portion.

8. The method of claim 1, wherein a portion of at least two of the opposing side panels is held onto the vacuum zone, and a longitudinal fold is created in each of the at least two opposing side panels.

9. The method of claim 1, wherein the pant-like garment comprises a training pant.

10. The method of claim 1, wherein the pant-like garment comprises a swimpant.

11. The method of claim 1, wherein the pant-like garment has unbonded side pahels.

12. Apparatus for tucking a pair of opposing side panels onto a body portion of a pant-like garment, the apparatus comprising:
    at least one conveyor having at least one vacuum zone the at least one vacuum zone providing sufficient vacuum to hold the body portion in place along outer longitudinal edges of the at least one vacuum zone; and
    a mechanical tucking device for pushing the side panels onto the body portion while the vacuum is holding the body portion on the at least one conveyor, the mechanical tucking device comprising two opposing assemblies, each assembly including at least one tucking blade on a rotary paddle or at least one tucking blade conveyed along a track that guides the at least one tucking blade a distance alongside the at least one conveyor.

13. The apparatus of claim 12, wherein the at least one vacuum zone comprises an outer area adjacent each of the outer longitudinal edges, the outer areas each having a first vacuum, and an inner area between the outer areas, the inner area having a second vacuum lower than the first vacuum.

14. The apparatus of claim 12, wherein the at least one vacuum zone comprises an outer area adjacent each of the outer longitudinal edges, the outer areas each having a first vacuum, and an inner area between the outer areas, the inner area having a second vacuum higher than the first vacuum.

15. The apparatus of claim 12, wherein the at least one vacuum zone comprises a uniform vacuum across a transverse width of the at least one vacuum zone.

16. The apparatus of claim 12, wherein the at least one vacuum zone has a transverse width about equal to a desired folded transverse width of the garment.

17. The apparatus of claim 12, comprising an upper conveyor having an upper vacuum zone and a lower conveyor having a lower vacuum zone.

18. The apparatus of claim 17, wherein the upper conveyor and the lower conveyor diverge from one another and then converge toward one another along a machine direction path of the conveyors.

19. The apparatus of claim 12, wherein the track of each of the assemblies maintains the at least one tucking blade essentially parallel to the pant-like garment.

20. The apparatus of claim 12, wherein the track of each of the assemblies travels essentially parallel to the at least one conveyor and above the at least one conveyor.

21. The apparatus of claim 12, wherein the track of each of the assemblies travels essentially parallel to the at least one conveyor and below the at least one conveyor.

22. The apparatus of claim 12, further comprising a driven stacker assembly having at least two stacker finger units.

* * * * *